(12) United States Patent
Ries et al.

(10) Patent No.: US 7,164,951 B2
(45) Date of Patent: Jan. 16, 2007

(54) ELECTRICAL CONNECTOR ASSEMBLY HAVING INTEGRATED CONDUCTIVE ELEMENT AND ELASTOMERIC SEAL FOR COUPLING MEDICAL LEADS TO IMPLANTABLE MEDICAL DEVICES

(75) Inventors: Andrew J. Ries, Lino Lakes, MN (US); Jay Lahti, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 538 days.

(21) Appl. No.: 10/632,027

(22) Filed: Jul. 31, 2003

(65) Prior Publication Data

US 2005/0033138 A1    Feb. 10, 2005

(51) Int. Cl.
    *A61N 1/375*    (2006.01)
(52) U.S. Cl. ............................................. 607/37
(58) Field of Classification Search ........... 607/36–38; 439/909
    See application file for complete search history.

(56) References Cited

U.S. PATENT DOCUMENTS

| 4,898,173 | A |  | 2/1990 | Daglow et al. |
| 5,252,090 | A |  | 10/1993 | Giurtino et al. |
| 5,261,395 | A |  | 11/1993 | Oleen et al. |
| 5,413,595 | A | * | 5/1995 | Stutz, Jr. ..................... 607/37 |
| 5,730,628 | A |  | 3/1998 | Hawkins |
| 5,843,141 | A | * | 12/1998 | Bischoff et al. ............... 607/37 |
| 6,430,442 | B1 | * | 8/2002 | Peters et al. .................. 607/37 |
| 2004/0034393 | A1 | * | 2/2004 | Hansen et al. ................ 607/37 |
| 2004/0167582 | A1 | * | 8/2004 | Tvaska et al. ................ 607/37 |

* cited by examiner

*Primary Examiner*—Robert E. Pezzuto
*Assistant Examiner*—Kristen Mullen
(74) *Attorney, Agent, or Firm*—Michael C. Soldrer; Girma Wolde-Michael

(57) ABSTRACT

An electrical connector assembly for facilitating electrical connection between a medical lead and circuitry of an implantable medical device (IMD). The electrical connector assembly integrates a conductive element with an elastomeric seal in order to achieve a simplified structure for electrically coupling of a lead to circuitry of the IMD and also providing a hermetic seal, and facilitates simplified and improved electrical coupling of a medical lead to circuitry of the IMD.

14 Claims, 8 Drawing Sheets

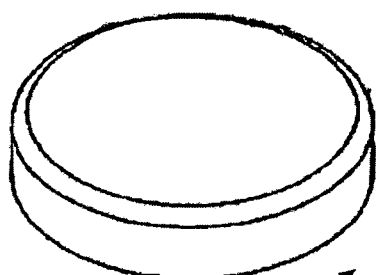
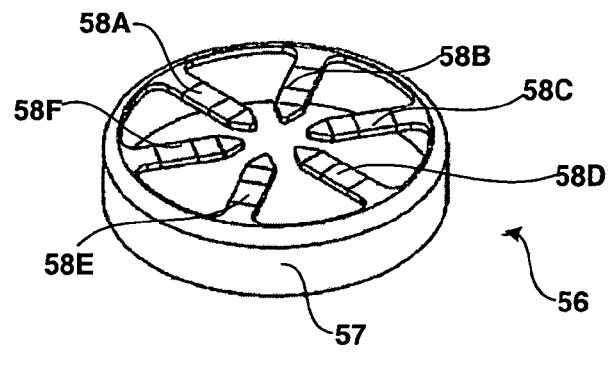
FIG. 12  FIG. 13
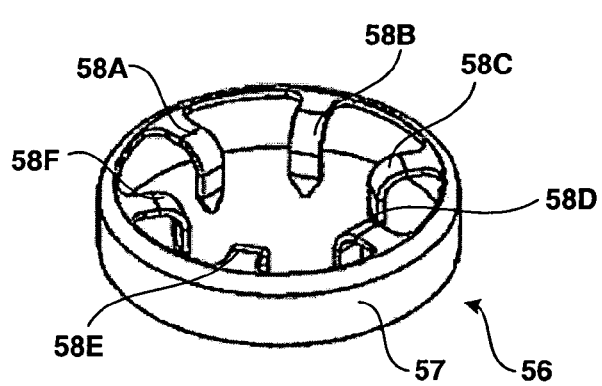
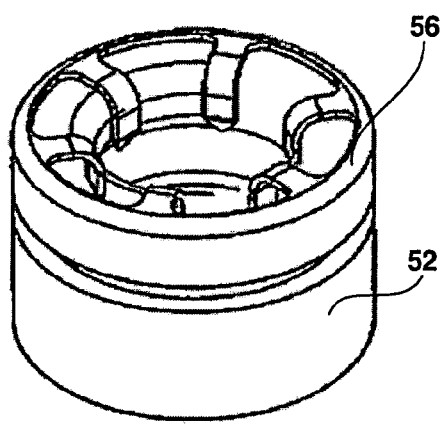
FIG. 14  FIG. 15

ELECTRICAL CONNECTOR ASSEMBLY HAVING INTEGRATED CONDUCTIVE ELEMENT AND ELASTOMERIC SEAL FOR COUPLING MEDICAL LEADS TO IMPLANTABLE MEDICAL DEVICES

CROSS-REFERENCE TO RELATED APPLICATIONS

Cross-reference is hereby made to commonly assigned related U.S. application Ser. No. 10/632,026, entitled "CONNECTOR ASSEMBLY FOR CONNECTING A LEAD AND AN IMPLANTABLE MEDICAL DEVICE", U.S. application Ser. No. 10/632,058,entitled "SMALL FORMAT CONNECTOR CLIP OF AN IMPLANTABLE MEDICAL DEVICE", and U.S. application Ser. No. 10/632,028, entitled "CONNECTOR ASSEMBLY FOR CONNECTING A LEAD AND AN IMPLANTABLE MEDICAL DEVICE", filed concurrently and herewith and incorporated herein by reference in their entirety.

TECHNICAL FIELD

The invention relates to medical leads of implantable medical devices (IMDs) and, more particularly, to electrical connectors that facilitate electrical coupling between the medical leads and circuitry of the IMD.

BACKGROUND

In the medical field, leads are used with a wide variety of medical devices. For example, leads are commonly implemented to form part of implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads position the electrodes with respect to various cardiac locations so that the pacemaker can deliver pulses to the appropriate locations. Leads are also used for sensing purposes, or both sensing and stimulation purposes.

In addition, leads are used in neurological devices such as deep-brain stimulation devices, and spinal cord stimulation devices. In that case, the leads are stereotactically probed into the brain to position electrodes for deep brain stimulation. Leads are also used with a wide variety of other medical devices, including devices that provide muscular stimulation therapy, devices that sense chemical conditions in a patient's blood, and the like. In short, medical leads can be used for sensing purposes, stimulation purposes, or both.

One challenge in implementing medical leads in an implantable medical device (IMD) is the electrical coupling between a respective lead and sensing or stimulation circuitry of the IMD. An IMD typically includes one or more leads, a housing that houses circuitry of the IMD, and a connector module that couples the leads to the circuitry. In particular, the connector module typically includes electrical contact structures for coupling a medical lead to circuitry within the housing of the IMD so that therapeutic simulation can be provided through the lead, or sensed conditions can be recorded by the circuitry. In addition, the connector module includes seal rings that provide hermetic barriers between the electrical contact structures. The leads are inserted into the connector module in order to achieve such electrical coupling between the lead and the circuitry of the IMD.

Various connection standards have been developed in order to ensure electrical connections between the IMD circuitry and the medical lead are acceptable, while also maintaining a sufficient hermetic seal between the connector module and the lead to avoid ingress of body fluids into the housing. These standards continue to evolve in order to accommodate new lead designs, such as in-line leads that include a plurality of electrodes and a plurality of electrical contact areas disposed along the lead.

There remains a need for lead connector configurations that are simple to use and inexpensive to fabricate. Improved simplicity can help ensure that physicians can make the electrical connections during implantation of the IMD with minimal concern for electrical coupling malfunction. Reduced fabrication expense can help ensure that patient costs associated with an IMD are minimized.

SUMMARY

In general, the invention is directed to electrical connector assemblies for facilitating electrical connection between a medical lead and circuitry of an implantable medical device (IMD). Various embodiments are directed toward an electrical connector assembly, an IMD, a connector module for an IMD, and methods of fabricating an electrical connector assembly of an IMD. For example, the electrical connector assembly described herein integrates a conductive element with a elastomeric seal in order to achieve a simplified structure for electrically coupling a lead to circuitry of the IMD while also providing a hermetic seal.

In one embodiment, the invention provides an electrical connector assembly for a medical device comprising an elastomeric element defining a hole to receive a portion of a medical lead, and a conductive element conforming to an end of the elastomeric element such that upon insertion of the medical lead through the hole, the conductive element electrically couples to an electrical contact element of the medical lead.

In another embodiment, the invention provides a connector module for an implantable medical device comprising a structure formed with a channel to receive a medical lead, the structure defining an access hole to the channel, and an electrical connector assembly positioned in the channel. The electrical connector assembly includes an elastomeric element defining a hole to receive a portion of a medical lead, and a conductive element conforming to an end of the elastomeric element such that upon insertion of the medical lead through the hole, the conductive element electrically couples to an electrical contact element of the medical lead.

In another embodiment, the invention provides an implantable medical device comprising a housing, circuitry within the housing, a connector module connected to the housing and including a structure formed with a channel and defining an access hole to the channel, a medical lead in the channel, and an electrical connector assembly positioned in the channel. The electrical connector assembly includes an elastomeric element defining a hole to receive a portion of a medical lead, and a conductive element conforming to an end of the elastomeric element such that upon insertion of the medical lead through the hole, the conductive element electrically couples to an electrical contact element of the medical lead.

In another embodiment, the invention provides a method comprising forming a conductive element, forming an elastomeric element to include a seal ring inside a hole, and assembling the conductive element to an end of the elastomeric element to form electrical connector assembly with an integrated seal.

Additional details of various embodiments are set forth in the accompanying drawings and the description below. Other features, objects and advantages will become apparent from the description and drawings, and from the claims.

BRIEF DESCRIPTION OF DRAWINGS

FIGS. 12–15 are perspective views illustrating fabrication of an electrical connector assembly as described herein.

DETAILED DESCRIPTION

The invention is directed to electrical connector assemblies for facilitating electrical connection between a medical lead and circuitry of an implantable medical device (IMD). The electrical connector assembly described herein integrates a conductive element with an elastomeric seal in order to achieve a simplified structure for electrically coupling a lead to circuitry of the IMD and also to achieve a good hermetic seal. The electrical connector assembly includes an elastomeric element formed with a hole to mate with a portion of medical lead, and a conductive element conforming to an end of the elastomeric element such that upon insertion of the medical lead through the hole, the conductive element electrically couples to the medical lead. The invention achieves improved electrical coupling and can reduce fabrication costs associated with production of an implantable medical device.

Figure 1:
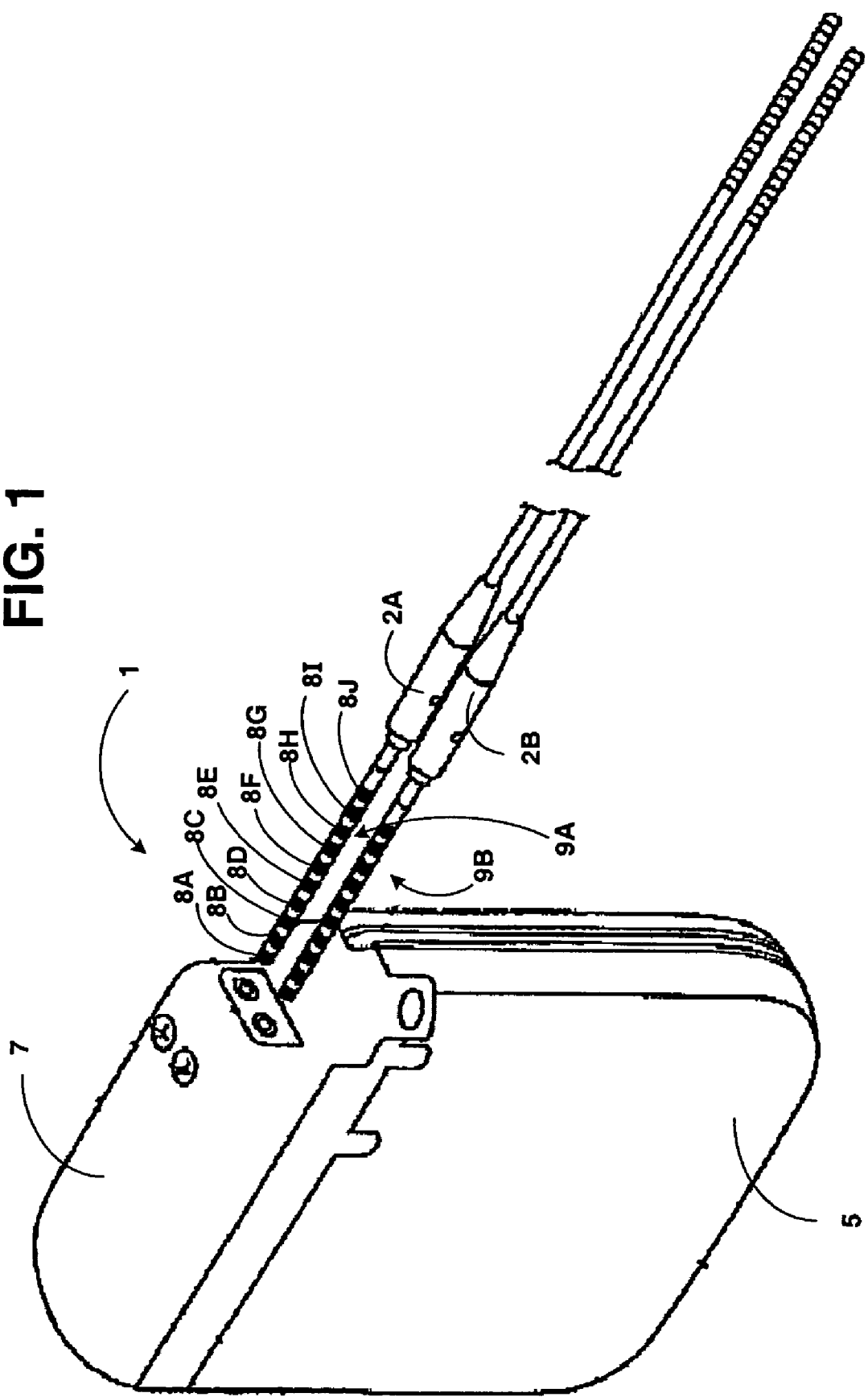
FIG. 1 is a perspective view of an implantable medical device (IMD) that can incorporate various aspects of the invention.

FIG. 1 is a perspective view of an IMD 1 that includes one or more medical leads 2A, 2B (collectively leads 2). In general, IMD 1 includes a housing 5 that houses IMD circuitry, one or more leads 2A, 2B that can be implanted in a patient, and a connector module 7 that receives proximal ends 9A, 9B of leads 2 to couple leads 2 to the circuitry in housing 5.

As illustrated in FIG. 1 with respect to lead 2A, the proximal end 9A of lead 2A includes a plurality of electrical contact areas 8A–8J (collectively contact areas 8). The invention facilitates electrical coupling to one or more of contact areas 8 within connector module 7. Moreover, the invention improves such contact for inline configurations like FIG. 1 in which a plurality of electrical contact areas 8 are positioned axially along a length of lead 2A. In particular, the invention may allow size reductions of contact areas 8 by improving electrical coupling assemblies that electrically interface with contact areas 8 inside connector module 7. For example, the invention integrates an elastomeric hermetic seal with a conductive electrical contact element in order to achieve such size reductions.

IMD 1 may correspond to any medical device that includes medical leads and circuitry coupled to the medical leads. By way of example, IMD 1 can take the form of an implantable cardiac pacemaker that provides therapeutic stimulation to the heart. Alternatively, IMD 1 may take the form of an implantable cardioverter or an implantable defibrillator, or an implantable cardiac pacemaker-cardioverter-defibrillator. In those cases, IMD 1 delivers pacing, cardioversion or defibrillation pulses to a patient via electrodes disposed on distal ends of leads 2. In other words, leads 2 position electrodes with respect to various cardiac locations so that IMD 1 can deliver pulses to the appropriate locations.

Alternatively, IMD 1 may correspond to a patient monitoring device, or a device that integrates monitoring and stimulation features. In those cases, leads 2 can include sensors disposed on distal ends of the respective lead for sensing patient conditions. The sensors can comprise electrical sensors, electrochemical sensors, pressure sensors, flow sensors, acoustic sensors, optical sensors, or the like. In many cases, IMD 1 performs both sensing and stimulation functions.

In still other applications, IMD 1 may correspond to a neurological device such as a deep-brain stimulation device or a spinal cord stimulation device. In those cases, leads 2 can be stereotactically probed into the brain to position electrodes for deep brain stimulation or into the spine for spinal stimulation. In other applications, IMD 1 provides muscular stimulation therapy, blood sensing functions, and the like. In short, IMD 1 may correspond to any of a wide variety of medical devices that implement leads and circuitry coupled to the leads.

As outlined in greater detail below, connector module 7 incorporates a connector assembly that improves and simplifies electrical coupling between leads 2 and circuitry in housing 5. More specifically, electrical connector assemblies integrating an elastomeric element with a conductive element are described which can provide an improved conductive interface between a medical lead and IMD circuitry. In addition, the invention may reduce fabrication costs associated with production of IMD 1. The described connector assemblies integrate an elastomeric seal with the conductive electrical contact element, thereby avoiding the need for separate fluid seals between conductive contact elements within connector module 7. Moreover, in addition to forming a seal, the elastomeric material also provides a biasing structure that tends to bias the conductive electrical contact element against an inserted medical lead for improved electrical interconnection.

Figure 2:
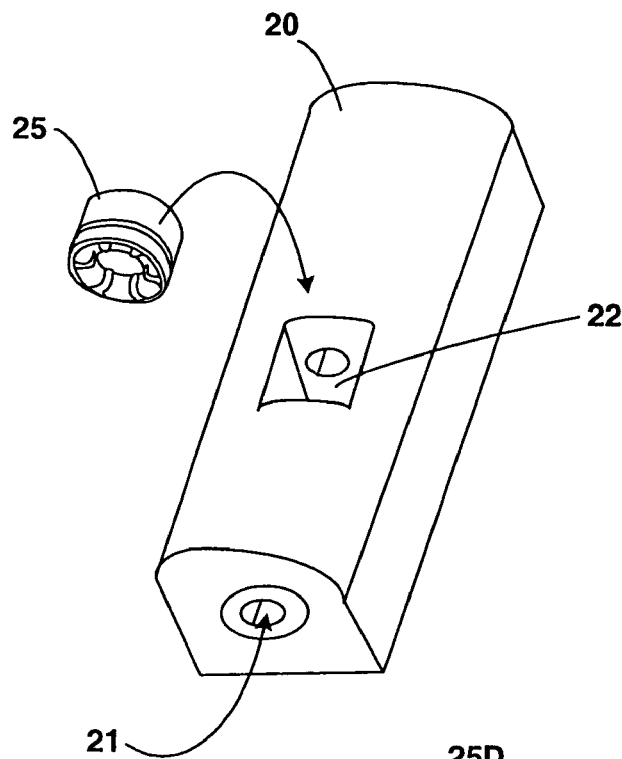
FIG. 2 is an exploded perspective view of components of a connector module of an IMD according to an embodiment of the invention.

FIG. 2 is an exploded perspective view of components that form at least part of a connector module 7 of an IMD 1. In particular, a connector block structure 20 is formed with an access hole 22 for receiving an electrical connector assembly 25 as described herein. Access hole 22 provides access to channel 21, and is sized to receive electrical connector assembly 25 so that electrical connector assembly 25 can electrically interface with electrical contacts carried by a lead inserted into channel 21.

As described herein, electrical connector assembly 25 integrates a conductive element with an elastomeric seal in order to achieve a simplified structure. Accordingly, the need for a separate seal and another access hole in connector bock structure 20 can be eliminated. In operation, a physician inserts a lead tip into channel 21. The lead tip passes through channel 21 so an electrical contact area carried by the lead tip is brought into alignment with a conductive element of electrical connector assembly 25, which is positioned inside access hole 22. A seal ring of electrical connector assembly 25 biases against the inserted lead to provide a fluid seal.

Figure 3:
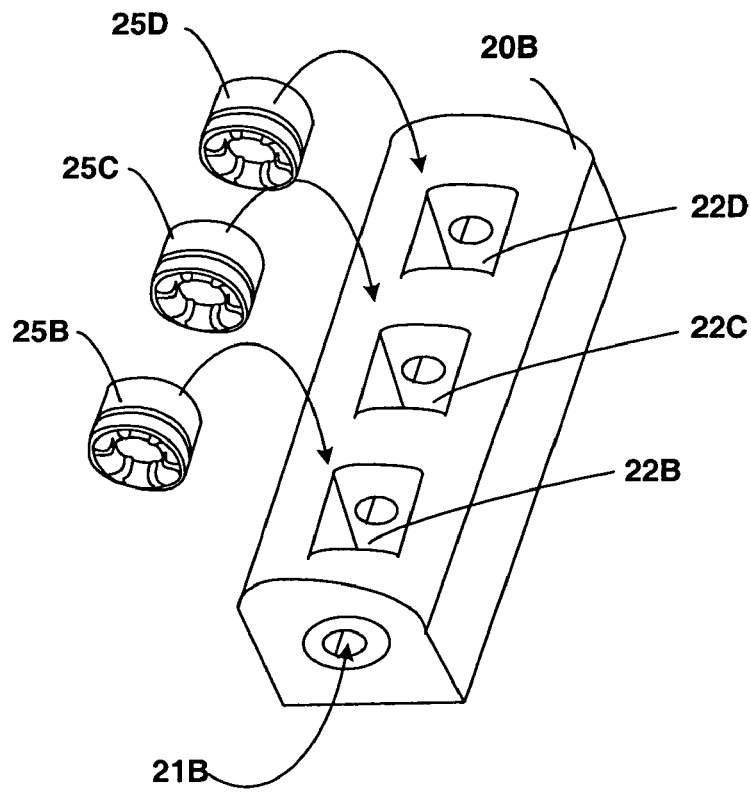
FIGS. 3 and 4 are exploded perspective views of components of connector modules of an IMD according to additional embodiments of the invention.
Figure 4:
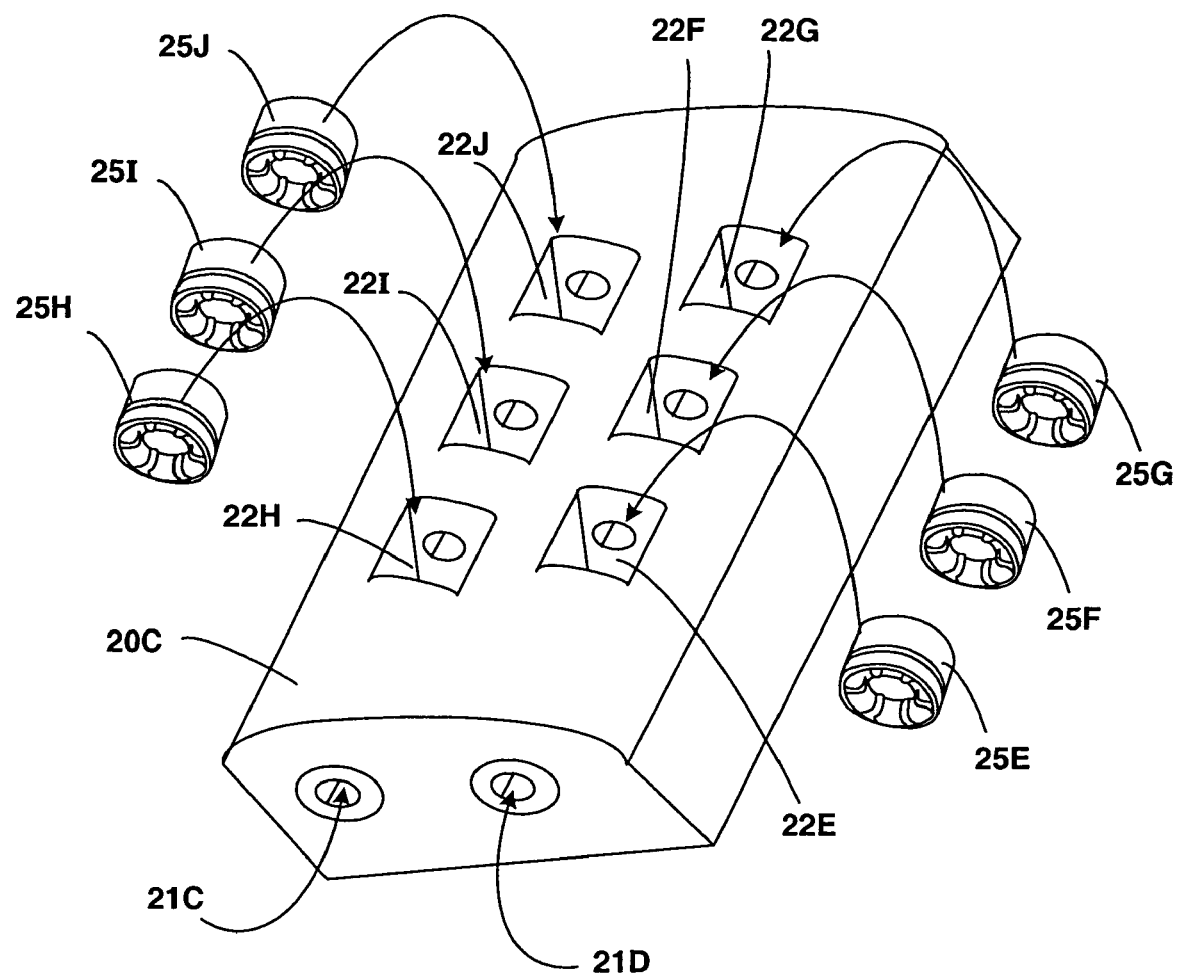

The components illustrated in FIG. 2 can provide a number of advantages. For example, because electrical connector assembly 25 is oriented perpendicular to channel 21, successive electrical connections can be placed very close to one another. In other words, the invention can allow the pitch or "spacing" between adjacent electrodes disposed axially along the lead tip to be reduced, permitting an increased density of electrical interconnections. Accordingly, the invention is particularly useful for in-line lead systems, i.e., systems in which the medical lead includes a number of electrical contacts disposed along axial positions of the lead. In that case, structure 20 could include a number of access holes 22. FIGS. 3 and 4 illustrate two such examples.

In particular, FIG. 3 illustrates a connector block structure 20B that includes a number of access holes 22B–22D disposed along channel 21B. A number of electrical connector assemblies 25B–25D, such as described in greater detail below, can be positioned in holes 22B–22D so that upon insertion of a medical lead into channel 21B, various in-line electrical contact surfaces of the lead couple with electrical connector assemblies 25B–25D. Moreover, because electrical connector assemblies 25B–25D also incorporate fluid seals, the need for separate seals can be avoided, which can allow for reduced pitch or "spacing" between adjacent electrical contact surfaces disposed axially along the lead.

FIG. 4 illustrates yet another connector block structure 20C that includes a number of access holes 22E–22J disposed respectively along channels 21C, 21D. In other words, connector block structure 20C is formed with two channels 21C, 21D for receiving two separate leads. In this example, each channel 21C, 21D includes three access holes 22E–22G and 22H–22J. Each hole 22E–22J receives one of the electrical connector assemblies 25E–25J, as described herein. Numerous other connector block structures could also be used with electrical connector assemblies, as described herein, e.g., making use of any number of channels and any number of access holes for receiving any number of electrical connector assemblies.

Another advantageous feature of electrical connector assembly 25 (FIG. 2) is the incorporation of a conductive electrical contact surface and an elastomeric seal into a common assembly. Accordingly, the need for separate fluid seals between conductive contact elements of connector module 7 (FIG. 1) can be avoided. Such features can improve electrical coupling of leads to the circuitry of IMD 1, and may also reduce fabrication costs associated with production of IMD 1.

In accordance with various embodiments, the connector block structure 20 of FIG. 2 may be oriented in any direction within connector module 7 (FIG. 1). For example, connector block structure 20 may be oriented with access hole 22 at the top of connector module 7, or at the bottom of connector module 7. In the latter case, electrical connector assembly 25 is inserted upward through the bottom of connector module 7 and connector module 7 is attached to housing 5 during assembly of IMD 1. Other arrangements, however, could also be used in accordance with the invention. For example, connector block structure 20 can be entirely enclosed within connector module 7, or could be arranged such that access hole 22 is accessible through the top of connector module. In the latter case, hole 22 may be covered with silicone, or the like, during assembly of IMD 1.

In any case, connector block structure 20 forms at least part of connector module 7 (FIG. 1) and defines a channel 21 to receive a proximal end of a medical lead. Electrical connector assembly 25 can be inserted into access hole 22 during fabrication, e.g., prior to insertion of the medical lead into channel 21.

Figure 5:
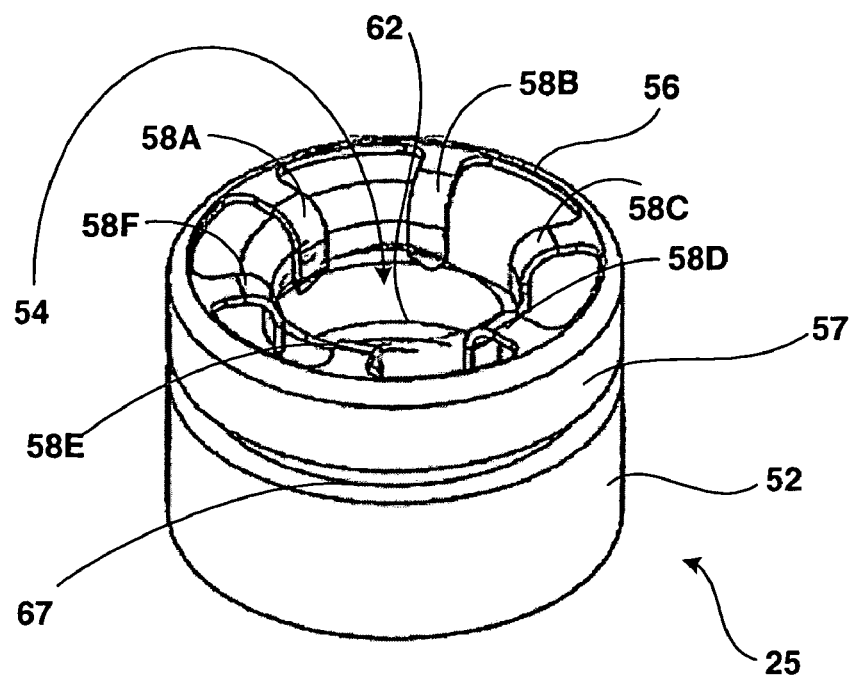
FIG. 5 is a perspective view of an electrical connector assembly according to an embodiment of the invention.
Figure 6:
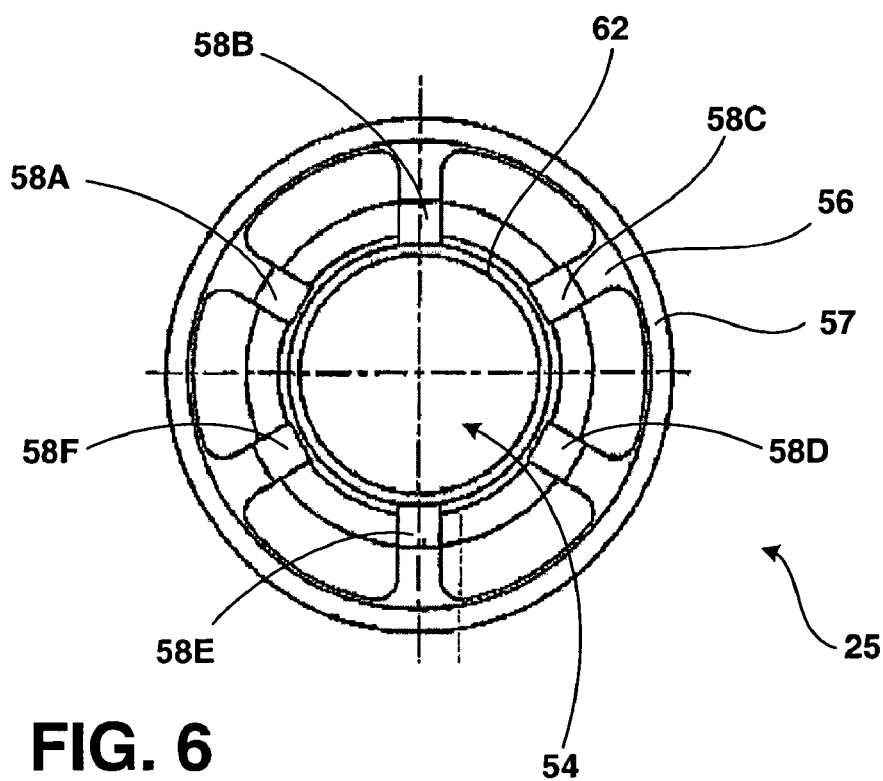
FIG. 6 is a top view of electrical connector assembly illustrated in FIG. 5.

FIG. 5 is a perspective view of electrical connector assembly 25 comprising an elastomeric element 52 formed with a hole 54 to mate with a portion of a medical lead. FIG. 6 is a top view of electrical connector assembly 25. Electrical connector assembly 25 includes a conductive element 56 conforming to an end of elastomeric element 52 such that upon insertion of the medical lead through hole 54, the conductive element 56 electrically couples to the medical lead. Elastomeric element 52 is formed with a seal ring 62 inside hole 54 in order to bias against an inserted lead and thereby provide a hermetic barrier. In addition, channel 67 formed can be formed in elastomeric element 52, e.g., for receiving a rigid outer ring (not shown in FIG. 5) to abut conductive element 56.

In the example of FIG. 5, conductive element 56 comprises a conductive ring 57 with tab-like elements 58A–58F extending radially inward from the ring. The conductive ring 57 fits about the end of the elestomeric element 52, and tab-like elements 58A–58F are bent to conform to an inner surface of hole 54. Accordingly, conductive element 56 conforms to the edge of elastomeric element 52 so that when a lead is inserted through hole 54 the lead contacts tab-like elements 58A–58F and elastomeric element 52 biases tab-like elements 58A–58F against the lead in order to ensure a good electrical interface. Once assembled into a connector block structure, such as illustrated in FIGS. 2–4, conductive ring 57 of conductive element 56 forms the electrical contact surface that electrically couples a lead to circuitry within IMD 1. For example, electrical wires that connect to circuitry within IMD 1 can be welded or otherwise coupled to conductive ring 57 or order to complete the electrical path from a lead 2 to the IMD 1 through connector module 7.

Figure 7:
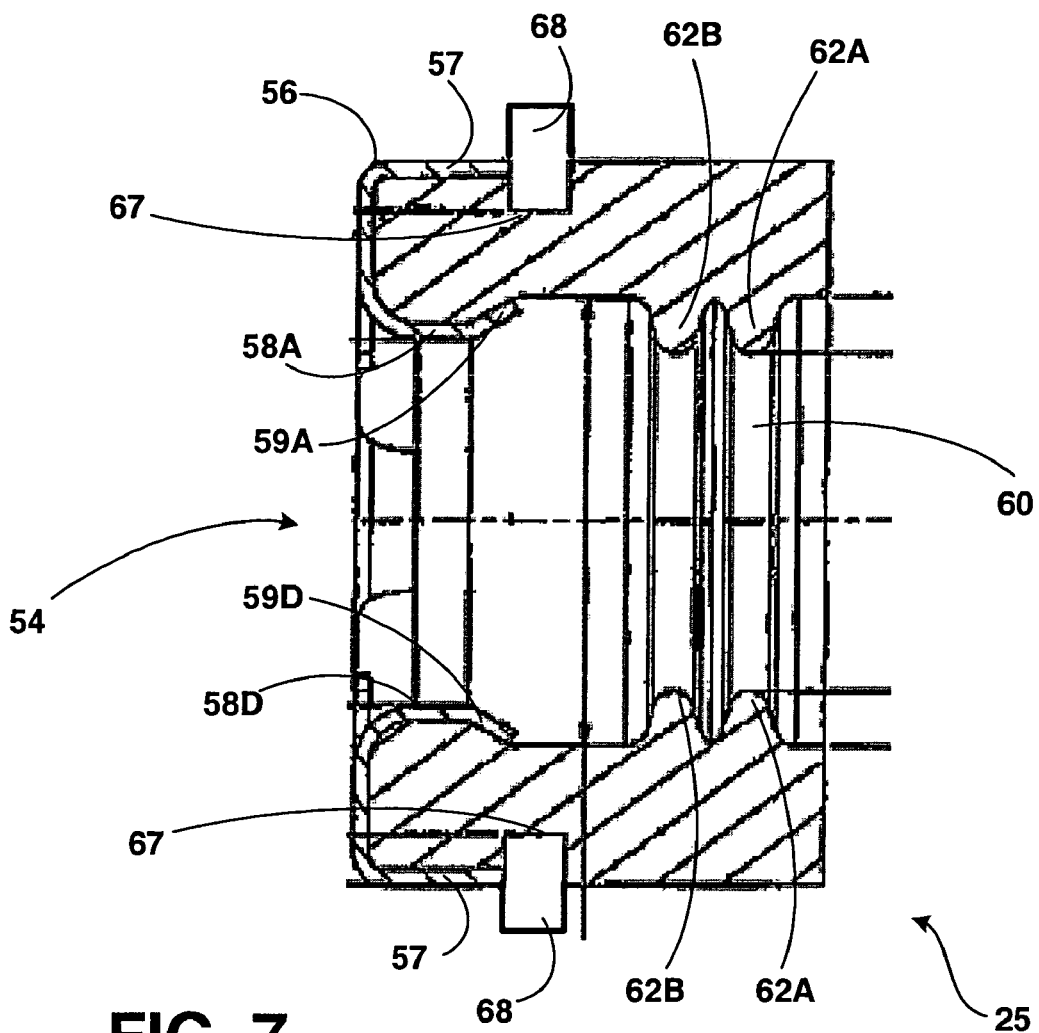
FIG. 7 is a cross-sectional side view of an electrical connector assembly and a portion of a medical lead inserted through the electrical connector assembly according to an embodiment of the invention.

FIG. 7 is a cross sectional side view of electrical connector assembly 25 and a portion of a medical lead 60 inserted through electrical connector assembly 25. Again, electrical connector assembly 25 comprises an elastomeric element 52 formed with a hole 54 to mate with a portion of medical lead 60. Conductive element 56 conforms to an end of elastomeric element 52 such that, upon insertion of medical lead 60 through hole 54, the conductive element 56 electrically couples to medical lead 60. Elastomeric element 52 is formed with one or more seal rings 62A, 62B inside hole 54 in order to bias against an inserted lead and thereby provide a hermetic barrier. In other words, seal rings 62A, 62B comprise elastomeric material extending radially inward with respect to hole 54 such that, when medical lead 60 is inserted through hole 54, seal rings 62A, 62B mechanically abut medical lead 60 to form a hermetic barrier.

As illustrated in FIG. 7, conductive element 56 comprises a conductive ring 57 with tab-like elements 58A, 58D extending radially inward from ring 57. The conductive ring 57 fits about the end of the elastomoeric element 52, and tab-like elements 58A, 58D are bent to conform to an inner surface of hole 54. Accordingly, conductive element 56 conforms to the edge of elastomeric element 52 so that when a lead is inserted through hole 54 the lead contacts tab-like elements 58A–58F and elastomeric element 52 biases tab-like elements 58A–58F against the lead in order to ensure a good electrical interface.

Figure 8:
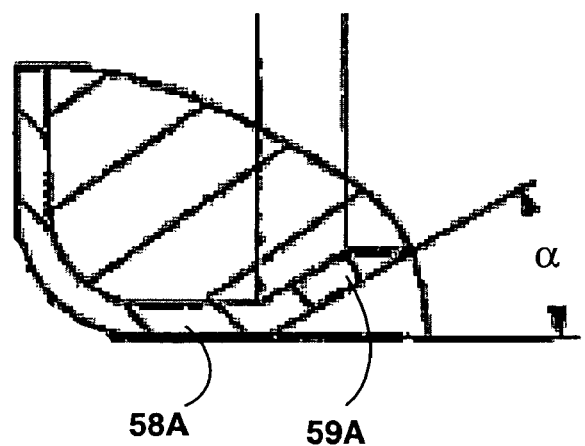
FIG. 8 is a cross-sectional side view of a distal tip of a tab-like element of a conductive element that forms part of the electrical connector assembly.

Moreover, distal tips 59A, 59D of tab-like elements 58A, 58D are bent toward the elastomeric element such that the tab-like elements form J-like shapes, which conform to hole 54. When distal tips 59A, 59D of tab-like elements 58A, 58D are bent toward the elastomeric element such that the tab-like elements form J-like shapes, lead insertion and removal can be improved. In particular, because tab-like elements 58A, 58D are bent to form J-like shapes, distal tips 59A, 59D will not catch or snag on lead 60 during insertion or removal. FIG. 8 is a close up view of distal tip 59A of tab-like element 58A being bent toward elastomeric element 52 such that the tab-like element 58A forms a J-like shape, which conforms to the hole defined by electrical connector assembly 25. The angle □ defined by distal tip 59A may be in the range of 10–90 degrees, although the invention is not necessarily limited in that respect.

Also depicted in FIG. 7 is a rigid outer ring 68 positioned within a channel 67 formed in elastomeric element 52. Specifically, rigid outer ring 68 is positioned adjacent conductive element 56 so as to limit lateral movement of conductive element 56 upon insertion of lead 60. In other words, during insertion of lead 60, rigid outer ring 68 inhibits substantial give or movement of the end of elastomeric element 52, which resides under conductive element 56.

Figure 9:
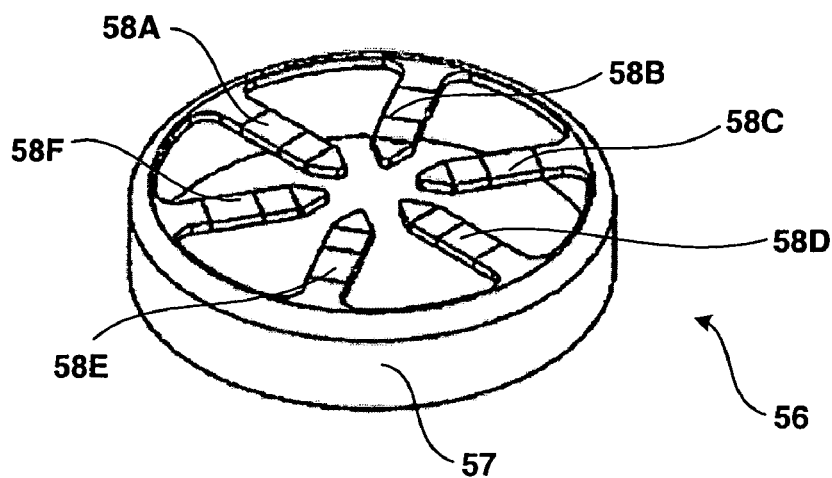
FIG. 9 is a perspective view of an exemplary conductive element comprising a conductive ring and conductive tab-like elements extending radially inward with respect to the conductive ring.
Figure 10:
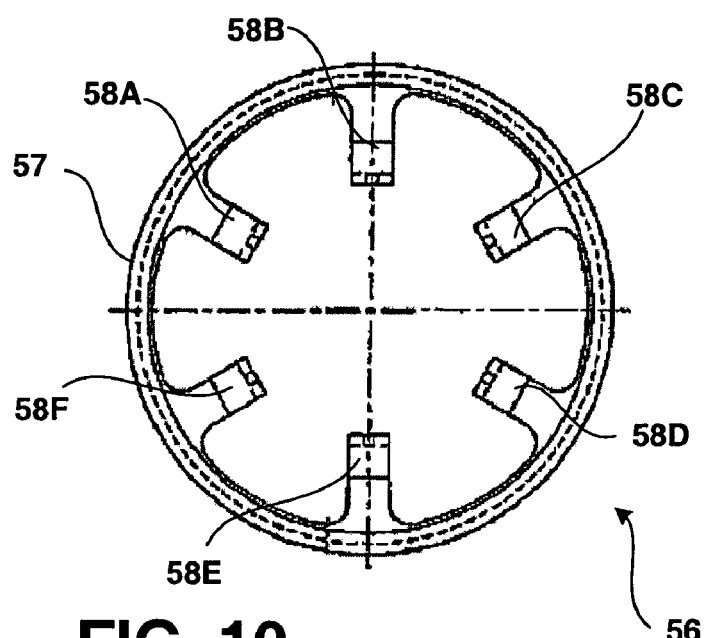
FIG. 10 is a top view of the conductive element with tab-like elements being bent inward at an approximately 90-degree angle relative to the position of tab-like elements shown in FIG. 9.
Figure 11:
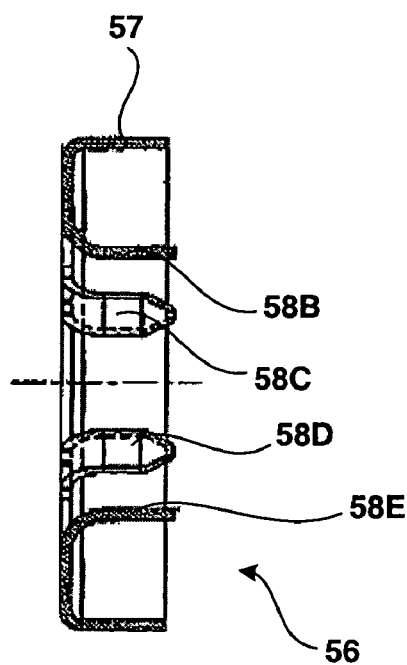
FIG. 11 is a side view of the conductive element illustrated in FIG. 10.

FIG. 9 is a perspective view of an exemplary conductive element 56 comprising a conductive ring 57 and conductive tab-like elements 58A–58F (collectively tab-like elements 58) extending radially inward with respect to conductive ring 57. FIG. 10 is a top view of conductive element 56, with tab-like elements 58 being bent inward at an approximately 90 degree angle relative to the position of tab-like elements 58 as shown in FIG. 8. FIG. 11 is a side view of conductive element 56, with tab-like elements 58 being bent inward at an approximately 90 degree angle relative to the position of tab-like elements 58 as shown in FIG. 9.

FIGS. 12–15 are perspective views illustrating fabrication of electrical connector assembly 25 as described herein. As shown in FIG. 12, a bottle-cap-like conductive element 111 is fabricated. Material is selectively removed from the interior of bottle-cap-like conductive element 111 to create conductive element 56 as shown in FIG. 13. Tab-like elements 58A–58F are then bent inward as illustrated in FIG. 14, and conductive element 56 is assembled to an edge of elastomeric element 52 to define the electrical connector assembly 25 illustrated in FIG. 15. In particular, connector assembly 25 incorporates a conductive element and an elastomeric seal ring 62.

Elastomeric element 52 may be injection molded to define hole 54 and elastomeric seal ring 62 within hole 54. In addition, channel 67 formed can be formed in elastomeric element 52, e.g., for receiving a rigid outer ring 68 to abut conductive element 56. During fabrication, the distal ends of tab-like elements 58A–58F bent towards elastomeric element 52 such that the distal tips form a J-like shape that conforms to hole 54, e.g., as shown in FIGS. 7 and 8.

Figure 16:
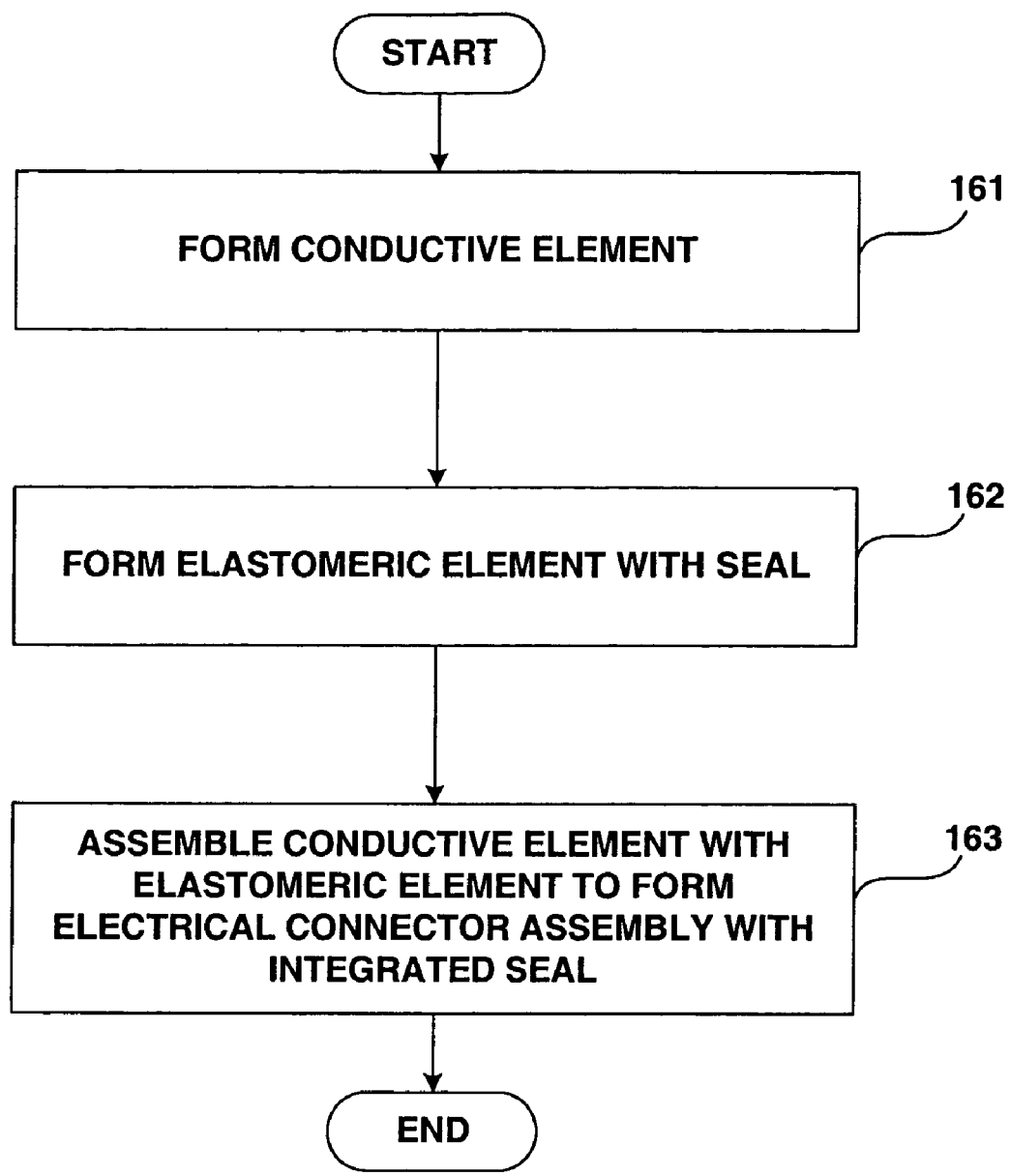
FIG. 16 is a flow diagram illustrating a process for fabricating an electrical connector assembly as described herein.

FIG. 16 is a flow diagram illustrating a process for fabricating electrical connector assembly 25 as described herein. As shown in FIG. 16, a conductive element 56 is formed (161), e.g., by creating a bottle-cap-like conductive element 111 and electively removed from the interior of bottle-cap-like conductive element 111 to create conductive element 56 as shown in FIG. 13. In addition, an elastomeric element 52 is formed to include a seal ring 62 within a hole 54 (162), e.g., by using injection molding techniques. The conductive element 56 is then assembled with the elastomeric element 52 to form an electrical connector assembly 56 that includes an integrated seal (163). The electrical connector assembly 56 can then be placed in a connector block structure 20 during assembly of IMD 1.

A number of embodiments and features have been described. These and other embodiments are within the scope of the following claims.

The invention claimed is:

1. An electrical connector assembly for a medical device comprising:

an elastomeric element forming a first hole to receive a portion of a medical lead;

a conductive element having a side wall extending from a proximal end to a distal end, an inner surface of the side wall forming a second hole, the conductive element fixedly positioned about an end of the elastomeric element so that the second hole is in fluid communication with the first hole; and a plurality of contact members extending from a contact member proximal end fixedly positioned along the proximal end of the side wall of the conductive element to a contact member distal end, the plurality of contact members extending inward through the second hole, the contact member distal end extending outward from the distal end of the side wall to be positioned within the first hole so that the contact member distal end is positioned against the elastomeric element upon insertion of the medical lead though the first hole and the second hole.

2. The electrical connector assembly of claim 1, wherein the elastomeric element is formed with a seal ring inside the second hole to bias against an inserted lead.

3. The electrical connector assembly of claim 1, wherein the contact member distal end is bent toward the elastomeric element such that the plurality of contact members form J-like shapes.

4. The electrical connector assembly of claim 1, wherein upon insertion of the medical lead through the first hole and the second hole, the elastomeric element biases the contact members against the medical lead.

5. A connector module for an implantable medical device comprising:

a connector block formed with a channel to receive a medical lead, the connector block forming an access hole to the channel;

an electrical connector assembly positioned in the channel;

an elastomeric element forming a first hole to receive a portion of a medical lead;

a conductive element having a side wall extending from a proximal end to a distal end, an inner surface of the side wall forming a second hole, the conductive element fixedly positioned about an end of the elastomeric element so that the second hole is in fluid communication with the first hole; and a plurality of contact members extending from a contact member proximal end fixedly positioned along the proximal end of the side wall of the conductive element to a contact member distal end, the plurality of contact members extending inward through the second hole, the contact member distal end extending outward from the distal end of the side wall to be positioned within the first hole so that the contact member distal end is positioned against the elastomeric element upon insertion of the medical lead though the first hole and the second hole.

6. The connector module of claim 5, wherein the elastomeric element is formed with a seal ring inside the second hole to bias against the medical lead following insertion of the medical lead through the hole.

7. The connector module of claim 5, wherein the contact member distal end is bent towards the elastomeric element such that the plurality of contact members form J-like shapes.

8. The connector module of claim 5, wherein upon insertion of the medical lead through the first hole and the second hole, the elastomeric element biases the contact members against the medical lead.

9. The connector module of claim 5, further comprising:
a plurality of access holes to the channel; and
a plurality of electrical connector assemblies positioned in the channel, wherein following insertion of the medical lead a plurality of in-line electrical contacts of the medical lead electrically couple respectively to the plurality of electrical connector assemblies.

10. An implantable medical device comprising:
a housing;
circuitry within the housing;
a connector module connected to the housing and including a structure formed with a channel and defining an access hole to the channel;
a medical lead in the channel;
an electrical connector assembly positioned in the channel;

an elastomeric element forming a first hole to receive a portion of a medical lead;

a conductive element having a side wall extending from a proximal end to a distal end, an inner surface of the side wall forming a second hole, the conductive element fixedly positioned about an end of the elastomeric element so that the second hole is in fluid communication with the first hole; and a plurality of contact members extending from a contact member proximal end fixedly positioned along the proximal end of the side wall of the conductive element to a contact member distal end, the plurality of contact members extending inward through the second hole, the contact member distal end extending outward from the distal end of the side wall to be positioned within the first hole so that the contact member distal end is positioned against the elastomeric element upon insertion of the medical lead though the first hole and the second hole.

11. The implantable medical device of claim 10, wherein the elastomeric element is formed with a seal ring inside the second hole to bias against the medical lead following insertion of the medical lead through the hole.

12. The implantable medical device of claim 10, wherein the contact member distal end is bent towards the elastomeric element such that the plurality of contact members form J-like shapes.

13. The implantable medical device of claim 10, wherein upon insertion of the medical lead through the first hole and the second hole, the elastomeric element biases the contact members against the medical lead.

14. The implantable medical device of claim 10, the connector module further comprising a plurality of access holes to the channel, and a plurality of electrical connector assemblies positioned in the channel, wherein following insertion of the medical lead a plurality of in-line electrical contacts of the medical lead electrically couple respectively to the plurality of electrical connector assemblies.

* * * * *